US006475806B1

(12) United States Patent
Benjamin et al.

(10) Patent No.: US 6,475,806 B1
(45) Date of Patent: *Nov. 5, 2002

(54) ANCHOR LIBRARIES AND IDENTIFICATION OF PEPTIDE BINDING SEQUENCES

(75) Inventors: Howard Benjamin, Lexington; Ethan Signer, Cambridge; Malcolm Gefter, Lincoln, all of MA (US)

(73) Assignee: Praecis Pharmaceuticals, Inc., Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 27 days.

(21) Appl. No.: 08/479,660

(22) Filed: Jun. 7, 1995

(51) Int. Cl.⁷ ............................................. G01N 33/543

(52) U.S. Cl. ....................................... 436/518; 530/300

(58) Field of Search ........................... 435/6, 320.1, 5; 530/300, 350; 436/518

(56) References Cited

U.S. PATENT DOCUMENTS

| | | | |
|---|---|---|---|
| 4,237,224 A | | 12/1980 | Cohen et al. |
| 4,293,652 A | | 10/1981 | Cohen |
| 4,338,397 A | | 7/1982 | Gilbert et al. |
| 4,362,867 A | | 12/1982 | Paddock |
| 4,366,246 A | | 12/1982 | Riggs |
| 4,394,443 A | | 7/1983 | Weisman et al. |
| 4,719,179 A | | 1/1988 | Barany |
| 4,959,312 A | | 9/1990 | Sirotkin |
| 5,202,418 A | * | 4/1993 | Lebl et al. .................. 530/334 |
| 5,223,409 A | | 6/1993 | Ladner et al. |
| 5,403,484 A | | 4/1995 | Ladner et al. |
| 5,571,698 A | | 11/1996 | Ladner et al. ............. 435/69.7 |
| 5,580,723 A | | 12/1996 | Wells et al. .................. 435/6 |
| 5,658,727 A | * | 8/1997 | Barbas et al. ................ 435/6 |
| 5,723,286 A | * | 3/1998 | Dower et al. ................. 435/5 |
| 5,744,354 A | * | 4/1998 | Lockerbie et al. .......... 435/325 |
| 5,750,373 A | | 5/1998 | Garrard et al. ............ 435/69.4 |
| 5,770,356 A | * | 6/1998 | Light, II et al. ............. 435/5 |
| 5,780,279 A | | 7/1998 | Matthews et al. ....... 435/172.3 |
| 5,821,047 A | | 10/1998 | Garrard et al. .............. 435/5 |
| 5,834,250 A | | 11/1998 | Wells et al. ................. 435/7.1 |
| 5,846,765 A | | 12/1998 | Matthews et al. ......... 435/69.1 |
| 5,872,207 A | * | 2/1999 | Morgan et al. ............. 530/300 |
| 6,372,425 B1 | * | 4/2002 | Arnold et al. ................ 435/5 |

FOREIGN PATENT DOCUMENTS

| | | |
|---|---|---|
| GB | 2183661 A | 6/1987 |
| WO | WO90/02809 | 3/1990 |
| WO | WO92/15677 | 9/1992 |
| WO | WO92/15679 | 9/1992 |

OTHER PUBLICATIONS

Hart et al., Cell Binding and Internalization by Filamentous Phage Displaying a Cyclic Arg–Gly–Asp–containing Peptide, Journal of Biol. Chem., 269(17):12468–12474, Apr. 29, 1994.

Lenstra et al., Isolation of sequences from a random–sequence expression library that mimic viral epitopes, Journal of Immunological Methods, 152:149–157 (1992).

N.B. Adey et al., "Characterization of phage that bind plastic from phage–displayed random peptide libraries", *Gene* 156:27–31 (1995).

H. Alexander et al., "Altering the antigenicity of proteins", *Proc. Natl. Acad. Sci. USA* 89:3352–3356 (1992).

M. Balass et al., "Identification of a hexapeptide that minics a conformation–dependent binding site of acetylcholine receptor by use of a phage–epitope library", *Proc. Natl. Acad. Sci. USA* 90:10638–10642 (1993).

C.F. Barbas III et al., "Assembly of combinatorial antibody libraries on phage surfaces: The gene III site", *Proc. Natl. Acad. Sci. USA* 88:7978–7982 (1991).

C.F. Barbas III, "Recent advances in phage display", *Curr. Opin. in Biotech.* 4:526–530 (1993).

J. Greenwood et al., "Multiple Display of Foreign Peptides on a Filamentous Bacteriophage", *J. Mol. Biol.* 220:821–827 (1991).

B.K. Kay et al., "An M13 phage library displaying random 38–amino–acid peptides as a source of novel sequences with affinity to selected targets", *Gene* 128:59–65 (1993).

S.F. Parmley and G.P. Smith, "Antibody–selectable filamentous fd phage vectors: affinity purification of target genes", *Gene* 73:305–318 (1988).

(List continued on next page.)

*Primary Examiner*—Ralph Gitomer
(74) *Attorney, Agent, or Firm*—Lahive & Cockfield, LLP; Giulio A. DeConti, Jr.; Maria Laccotripe Zacharakis

(57) ABSTRACT

An anchor library is described. A collection of recombinant vectors having a nucleic acid encoding a displayed peptide sequence is provided. The displayed peptide sequence of each of the vectors comprises $X^1(Y^1)_{c_1}X^2(Y^2)_{c_2}X^3(Y^3)_{c_3}X^4$, wherein each $X^1, X^2, X^3$ and $X^4$ is an amino acid residue and any of $X^1, X^2, X^3$ and $X^4$ can be the same or different from any one other, wherein each $Y^1, Y^2$ and $Y^3$ is alanine or glycine or a combination of alanine and glycine that is respectively $c^1, c^2$ and $c^3$ amino acid residues long and any of $Y^1, Y^2$ and $Y^3$ if present can be the same or different from any one other, wherein each of $c^1, c^2$ and $c^3$ is 0 to about 20, wherein $X^1$ and $X^4$ are each attached to an amino acid residue that flanks the displayed peptide sequence. Preferably, at least about $10^5$ to about $10^8$ permutations of all possible permutations of the displayed peptide sequence are present in the anchor library. Preferably, the library does not contain more than about 10% of displayed peptide sequences different from the first mentioned displayed peptide sequences. Also described are methods of making anchor libraries and methods of using anchor libraries to identify a peptide sequence that binds to a target. Recombinant vectors, filamentous phage, nucleic acid molecules and proteins are also provided.

42 Claims, No Drawings

OTHER PUBLICATIONS

J.D. Marks et al., "Human Antibody Fragments Specific for Human Blood Group Antigens from a Phage Display Library", *Bio/Technology* 11:1145–1149 (1993).

S. Blond–Elguindi et al., "Affinity Panning of a Library of Peptides Displayed on Bacteriophages Reveals the Binding Specificity of BiP", *Cell* 75:717–728 (1993).

M.A. McLafferty et al., "M13 bacteriophage displaying disulfide–constrained microproteins", *Gene* 128:29–36 (1993).

J.M. Ostresh et al., "Libraries from libraries: Chemical transformation of combinatorial libraries to extend the range and repertoire of chemical diversity", *Proc. Natl. Acad. Sci. USA* 91:11138–11142 (1994).

C.F. Barbas III et al., "High–affinity self–reactive human antibodies by design and selection: Targeting the integrin ligand binding site", *Proc. Natl. Acad. Sci. USA* 90:10003–10007 (1993).

J. K. Scott et al., "A family of concanavalin A–binding peptides from a hexapeptide epitope library", *Proc. Natl. Acad. Sci. USA* 89:5398–5402 (1992).

J.J. Devlin et al., "Random Peptide Libraries: A Source of Specific Protein Binding Molecules", *Science* 249:404–406 (1990).

W. Markland et al., "Design, construction and function of a multicopy display vector using fusions to the major coat protein of bacteriophage M13", *Gene* 109:13–19 (1991).

D. Medynski, "Phage Display: All Dressed Up and Ready to Role", *Bio/Technology* 12:1134–1136 (1994).

S.E. Cwirla et al., "Peptides on phage: A vast library of peptides for identifying ligands", *Proc. Natl. Acad. Sci. USA* 87:6378–6382 (1990).

D. Roberts et al., "Antibody as a surrogate receptor in the screening of a phage display library", *Gene* 128:67–69 (1993).

S. Brenner and R.A. Lerner, "Encoded combinatorial chemistry", *Proc. Natl. Acad. Sci. USA* 89:5381–5383 (1992).

A.W. Yem et al., "Biotinylation of Reactive Amino Groups in Native Recombinant Human Interleukin–1β", *J. Biol. Chem.* 264(30):17691–17697 (1989).

J. Slack et al., "Application of the Multiscreen System to Cytokine Radioreceptor Assays", *Bio Techniques* 7(10):1132–1138 (1989).

F. Breitling et al., "A surface expression vector for antibody screening", *Gene* 104:147–153 (1991).

F. Felici et al., "Mimicking of discontinuous epitopes by phage–displayed peptides, II. Selection of clones recognized by a protective monoclonal antibody against the *Bordetella pertussis* toxin from phage peptide libraries", *Gene* 128:21–27 (1993).

G.P. Smith and J.K. Scott, "Libraries of Peptides and Proteins Displayed on Filamentous Phage", *Meth. Enzymology* 217:228–257 (1993).

J. Ku and P.G. Schultz, "Alternate protein frameworks for molecular recognition", *Proc. Natl. Acad. Sci. USA* 92:6552–6556 (1995).

R.J. Rickles et al., "Identification of Src, Fyn, Lyn, P13K and Abl SH3 domain ligands using phage display libraries", *The EMBO Journa l*13(23):5598–5604 (1994).

R.B. Christian et al., "Simplified Methods for Construction, Assessment and Rapid Screening of Peptide Libraries in Bateriophage", *J. Mol. Biol.* 227:711–718 (1992).

B.L. Roberts et al., "Directed evolution of a protein: Selection of potent neutrophil elastase inhibitors displayed on M13 fusion phage", *Proc. Natl. Acad. Sci. USA* 89:2429–2433 (1992).

R.J. Goodson et al., "High–affinity urokinase receptor antagonists identified with bacteriophage peptide display", *Proc. Natl. Acad. Sci. USA* 91:7129–7133 (1994).

B.P. Cormack and K. Struhl, "Regional Codon Randomization: Defining a TATA–Binding Protein Surface Required for RNA Polymerase III Transcription", *Science* 262:244–248 (1993).

J. Hammer et al., "Identification of a Motif for HLA–DR1 Binding Peptides Using M13 Display Libraries", *J. Exp. Med.* 176:1007–1013 (1992).

G.P. Smith et al., "A ribonuclease S–peptide antagonist discovered with a bacteriophage display library", *Gene* 128:37–42 (1993).

R.M. Wright et al., "Binding Epitope of Somatostatin Defined by Phage–Displayed Peptide Libraries", *Bio/Technology* 13:165–169 (1995).

R. Hoess et al., "Identification of a peptide which binds to the carbohydrate–specific monoclonal antibody B3", *Gene* 128:43–49 (1993).

J.K. Scott and G.P. Smith, "Searching for Peptide Ligands with an Epitope Library", *Science* 249:386–390 (1990).

R. Horuk, "A rapid and direct method for the detection and quantification of interleukin–1 receptors using 96 well filtration plates", *J. Immun. Methods* 119:255–258 (1989).

H.B. Lowman and J.A. Wells, "Monovalent Phage Display: A Method for Selecting Variant Proteins from Random Libraries", *Methods: A Companion to Methods in Enzymology* 3(3):205–216 (1991).

E. Söderlind et al., "Phage Display Technology in Antibody Engineering: Design of Phagemid Vectors and in vitro Maturation Systems", *Immun. Reviews* 130:109–124 (1992).

R.A. Houghten et al., "Peptide libraries: criteria and trends", *TIG* 9(7):235–239 (1993).

J.A. Wells et al., "Rapid evolution of peptide and protein binding properties in vitro", *Curr. Opin. Biotech.* 3:355–362 (1992).

L.S. Jespers et al., "Surface Expression and Ligand–Based Selection of cDNAs Fused to Filamentous Phage Gene IV", *Bio/Technology* 13:378–382 (1995).

E. Koivunen et al., "Selection of Peptides Binding to the $\alpha_5\beta_1$ Integrin from Phage Display Library", *J. Biol. Chem.* 268(27):20205–20210 (1993).

J.D. Marks et al., "Molecular Evolution of Proteins on Filamentous Phage", *J. Biol. Chem.* 267(23):16007–16010 (1992).

J.K. Scott, "Discovering peptide ligands using epitope libraries", *TIBS* 17:241–245 (1992).

L.B. Lyons et al., "The Genetic Map of the Filamentous Bacteriophage f1", *Virol.* 49:45–60 (1972).

N.F. Sepetov et al., "Library of Libraries: Approach to synthetic combinatorial library design and screening of pharmacophore motifs", *Proc. Natl. Acad. Sci USA* 92:5426–5430 (1995).

C. Swimmer et al., "Phage display of ricin B chain and its single binding domains: System for screening galactose––binding mutants", *Proc. Natl. Acad. Sci. USA* 89:3756–3760 (1992).

K.F. Wertman et al., "Host vector interactions which affect the viability of recombinant phage lambda clones", *Gene* 49:253–262 (1986).

E.J. Rebar and C.O. Pabo, "Zinc Finger Phage: Affinity Selection of Fingers with New DNA–Binding Specificities", *Science* 263:671–673 (1994).

V.J. Hruby et al., "Emerging approaches in the molecular design of receptor–selective peptide ligands: conformational, topographical and dynamic considerations", *Biochem. J.* 268:249–262 (1990).

G.D. Hurst et al., "Rapid and Economical Preparation of Oligonucleotide Libraries", at Exploiting Molecular Diversity Combinatorial Libraries for Drug Discovery, Jan. 12–14, 1994, San Diego, Calif.

L. Castagnoli et al., "Selection from a Peptide Library of the Antigenic Determinants of a Protein", Generation of Antibodies by Cell and Gene Immortalization, Terhorst C. et al. (eds.), Year Immunol. Basel, Karger, vol. 7, pp. 41–49 (1993).

J. Hammer et al., "Promiscuous and Allele–Specific Anchors in HLA–DR–Binding Peptides", *Cell* 74:197–203 (1993).

G. Smith, Manual: "Cloning in fuse vectors", University of Missouri, Division of Biological Sciences (Feb. 1992).

* cited by examiner

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO:1:

GGGCTGCCGG GNNKNNK                17

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

GGGCTGCCGG GNNKGSNNNK            20

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

```
GGGCTGCCGG GNNKGSNGSN NNK                                           23
```

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:4:

```
GGGCTGCCGG GNNKGSNGSN GSNNNK                                        26
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:5:

```
GGGCTGCCGG GNNKGSNGSN GSNGSNNNK                                     29
```

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:6:

```
GSNGSNGSNN NK                                                       12
```

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:7:

```
GSNGSNGSNG SNNNK                                                    15
```

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:8:

```
NNKGGTGGTG CTGCTG                                                   16
```

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:9:

```
GSNNNKGGTG GTGCTGCTG                                           19
```

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:10:

```
GSNGSNNNKG GTGGTGCTGC TG                                       22
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

```
GSNGSNGSNN NKGGTGGTGC TGCTG                                    25
```

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:12:

```
GSNGSNGSNG SNNNKGGTGG TGCTGCTG                                 28
```

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:13:

```
GGGCTGCCGG G                                                   11
```

(2) INFORMATION FOR SEQ ID NO:14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:14:

```
GGTGGTGCTG CTG                                                 13
```

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:15:

CCCGGCAGCC CCGT                                                                              14

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:16:

CAGCACCACC                                                                                   10

(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:17:

Xaa Thr Pro Trp Xaa Gln
1               5

(2) INFORMATION FOR SEQ ID NO:18:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:18:

GGGCTGCCGG GNNKNNKNNK NNKNNKNNKG GTGGTGCTGC TG                                                42

ANCHOR LIBRARIES AND IDENTIFICATION OF PEPTIDE BINDING SEQUENCES

FIELD OF THE INVENTION

This invention relates to anchor libraries and to methods of using anchor libraries to identify peptide sequences that bind to a target molecule.

BACKGROUND OF THE INVENTION

The identification of peptides which bind to target molecules which are involved in various physiological functions, can have significant implications for the diagnosis and/or treatment of various abnormal or diseased conditions. For example, a binding peptide might modulate the original activity of the target molecule and therefore be useful as a drug.

The use of standard libraries to identify peptide sequences which specifically bind to target molecules is generally limited to pre-existing natural sequences from the organism which is the source of the DNA. More recently, libraries have been described which have clones containing short synthetic random coding sequences. See, e.g., Scott and Smith, Science 249:386–390 (1990); Cwirla et al., Proc. Natl. Acad. Sci. USA 87:6378–6382 (1990); Devlin et al., Science 249:404–406 (1990). These libraries are mixtures of filamentous phage clones, each displaying a random peptide sequence on the virion surface. In these types of libraries, the random amino acids are contiguous. The size of the peptides that can be screened for binding peptides in such contiguous random amino acid libraries is limited, in that as the size of the peptides increases, at some point it is not feasible to adequately search such a library since there are too many clones required to cover all possible permutations of the random amino acids in the peptides.

SUMMARY OF THE INVENTION

It is an object of the invention to identify peptide sequences that bind to specific target molecules.

It is another object of the invention to identify amino acid residues in a peptide that are important contacts between the peptide and a target molecule.

It is another object of the invention to determine where amino acid residues in a peptide that are important contacts between the peptide and a target molecule, are best positioned within the peptide.

It is another object of the invention to use an anchor library in which the random amino acid residues of the library are not continuous, for identifying amino acid residues in a peptide that are important contacts between the peptide and a target molecule.

It is another object of the invention to use an anchor library in which the random amino acid residues of the library are distributed throughout a much larger peptide domain consisting of random glycine and/or alanine residues, for identifying amino acid residues in a peptide that are important contacts between the peptide and a target molecule.

It is another object of the invention to search large peptide phage display libraries of, e.g., 16 mers, for a reduced number of essential amino acid residue contacts, e.g., four, between the peptide and a target molecule.

It is another object of the invention to identify a consensus sequence of a defined number of amino acid residues in any configuration of spacer amino acids, that are important contacts between a peptide and a target molecule.

It is yet another object of the invention to use a known core binding sequence on a peptide which binds to a target molecule, and identify surrounding amino acid residues which are additional important contacts between the peptide and the target molecule.

Still another object of the invention is to identify cysteine residues on a peptide which can form disulfide bridges and thereby increase the binding affinity of the peptide with a target molecule.

According to the invention, an anchor library is provided. The anchor library comprises a collection of recombinant vectors, e.g., viruses, phage, e.g., filamentous phage, plasmids or cosmids. Each of the vectors has a nucleic acid sequence inserted in a gene, e.g., a coat protein gene, e.g., gene III or gene VIII, thioredoxin, staphnuclease, lac repressor, gal4 or an antibody. The nucleic acid sequence encodes a displayed peptide sequence, e.g., displayed on the surface of a virion, cell, spore or gene product, which comprises:

$$X^1(Y^1)_{c_1}X^2(Y^2)_{c_2}X^3(Y^3)_{c_3}X^4$$

wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively, $c^1$, $c^2$ and $c^3$ amino acid residues long and any of $Y^1$, $Y^2$ and $Y^3$ if present can be the same or different from any one other, wherein each of $c^1$, $c^2$ and $c^3$ preferably is 0 to about 20, more preferably is 0 to about 10, even more preferably is 0 to about 6, or most preferably is 0 to about 4, wherein $X^1$ and $X^4$ are each attached to an amino acid residue that flanks the displayed peptide sequence. In certain embodiments, at least about $10^5$ to about $10^8$ permutations of all possible permutations of the displayed peptide sequence are present in the anchor library. In other embodiments, the library does not contain more than about 10%, or more than about 1%, or more than about 0.1%, of displayed peptide sequences different from the first mentioned displayed peptide sequences.

Another aspect of the invention is where each $Y^1$, $Y^2$ and $Y^3$ is any specified amino acid or combination of specified amino acids, e.g., alanine or cysteine or a combination of alanine and cysteine; or glycine or cysteine or a combination of glycine and cysteine.

In certain embodiments, the displayed peptide sequence further has at least one core binding sequence which is preferably about 1 to about 20 amino acid residues in length, more preferably about 4 to about 10, and most preferably is 6. The core binding sequence can be in addition to, or a replacement for, other amino acids in the displayed peptide sequence. Variations include the presence of more than one core binding sequence in the displayed peptide sequence, where, e.g., the core binding sequences can be adjacent, or not adjacent, to each other, and where they can be, e.g., identical or not identical to each other.

In other embodiments, the displayed peptide sequence further has at least one constraint, e.g., a crosslink, e.g., a disulfide bond, e.g., from the presence of a cysteine residue; a stacking interaction; a positive or negative charge; hydrophobicity; hydrophilicity; a structural motif, e.g., a zinc finger formation, a leucine zipper, or a β-turn structure, e.g., from the presence of the sequence asp gly or pro gly; or combinations thereof. Cysteine residues can be in addition to, or a replacement for, other amino acids in the displayed peptide sequence.

Another aspect of the invention is a method of making an anchor library. A collection of nucleic acid sequences is synthesized. The nucleic acid sequences are inserted into vectors to give recombinant vectors and the recombinant vectors are introduced into a host. The host having the recombinant vectors is propagated so as to result in a collection of recombinant vectors, each of which has a nucleic acid sequence from the collection of nucleic acid sequences which encodes a displayed peptide sequence comprising:

$$X^1(Y^1)_{c^1}X^2(Y^2)_{c^2}X^3(Y^3)_{c^3}X^4.$$

Another aspect of the invention is a method of using an anchor library to identify a peptide sequence that binds to a target. An anchor library having a collection of recombinant vectors is provided. Each of the recombinant vectors has a nucleic acid sequence which encodes a displayed peptide sequence comprising:

$$X^1(Y^1)_{c^1}X^2(Y^2)_{c^2}X^3(Y^3)_{c^3}X^4.$$

Expression and display of the peptide sequence is permitted. The anchor library is contacted with the target, e.g., proteinaceous or non-proteinaceous molecules, e.g., ligands, receptors, hormones, cytokines, antibodies, antigens, enzymes, enzyme substrates or viruses, under conditions in which the displayed peptide sequence binds to the target, and the displayed peptide sequence which binds to the target is identified, e.g., by sequencing the nucleic acid sequence on the recombinant vector which encodes for the displayed peptide sequence. Preferably, the identified displayed peptide sequence is synthesized.

The invention also provides for a peptide which is identified by use of an anchor library, in which the peptide is useful as a diagnostic or therapeutic product in that the peptide is able to bind to a target molecule which is involved in a physiological process.

Other aspects of the invention include, e.g., a collection of recombinant DNA molecules encoding peptide sequences having a plurality of different binding domains; a recombinant filamentous phage having a displayed peptide sequence with known binding properties and which is foreign to the filamentous phage; a recombinant vector having a nucleic acid sequence inserted in a gene, the nucleic acid sequence encoding a displayed peptide sequence having known binding properties; a recombinant nucleic acid molecule having a nucleic acid sequence inserted in a gene, the nucleic acid sequence encoding a displayed peptide sequence having known binding properties; and a recombinant protein having a displayed peptide sequence having known binding properties.

The above and other objects, features and advantages of the present invention will be better understood from the following specification.

DETAILED DESCRIPTION

This invention provides an anchor library. The anchor library comprises a collection of recombinant vectors, each of which has a nucleic acid sequence inserted in a gene. The nucleic acid sequence encodes a displayed peptide sequence which comprises $$X^1(Y^1)_{c^1}X^2(Y^2)_{c^2}X^3(Y^3)_{c^3}X^4$$

wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively, $c^1$, $c^2$ and $c^3$ amino acids residues long and any of $Y^1$, $Y^2$ and $Y^3$ if present can be the same or different from any one other, wherein each of $c^1$, $c^2$ and $c^3$ is 0 to about 20, wherein $X^1$ and $X^4$ are each attached to an amino acid residue that flanks the displayed peptide sequence. In certain embodiments at least about $10^5$ to about $10^8$ permutations of all possible permutations of the displayed peptide sequence are present in the anchor library. In other embodiments, the library does not contain more than about 10%, or more than about 1%, or more than about 0.1% of displayed peptide sequences different from the first mentioned displayed peptide sequences.

By anchor library is meant a library in which the recombinant vectors have nucleic acid sequences which code for peptide sequences with random amino acids in which the random amino acids are not continuous. An anchor library is thus distinguishable from other random amino acid libraries in which all random amino acids in the peptide sequence of interest are contiguous. In anchor libraries, a given number of random amino acids are distributed throughout a larger peptide domain consisting of specifically designated amino acid residues. Anchor libraries are meant to include, e.g., external libraries, e.g., phage display libraries, and internal libraries, e.g., plasmid libraries. Chemical libraries can be anchor libraries.

Vectors are meant to include, e.g., phage, viruses, plasmids, cosmids, or any other suitable vector known to those skilled in the art. The vector has a gene, native or foreign, which is able to tolerate insertion of a foreign peptide into the gene product of the gene. By gene is meant an intact gene or fragment thereof. In the invention, the expressed gene product contains the inserted peptide.

For certain embodiments of this invention, e.g., where phage display libraries are employed, the preferred vectors are filamentous phage, though other vectors can be used. Filamentous phage are single stranded DNA phage having coat proteins. Preferably, the gene that the nucleic acid sequence is inserted into is a coat protein gene of the filamentous phage. Preferred coat proteins are gene III or gene VIII coat proteins. Insertion of a foreign peptide into a coat protein gene results in the display of the foreign peptide on the surface of the phage. Insertion into any other gene product in which the inserted peptide is displayed can also be used in this invention. Examples of filamentous phage vectors which can be used in this invention are fUSE vectors, e.g., fUSE1, fUSE2, fUSE3 and fUSE5, in which the insertion is just downstream of the pIII signal peptide. Smith and Scott, Methods in Enzymology 217:228–257 (1993).

In other embodiments, e.g., where internal libraries are employed, the preferred vectors are plasmids, though other vectors can be used. The gene that the nucleic acid is inserted into is a gene which also results in display of the inserted peptide sequence. The gene can encode for an exported or non-exported gene product. Preferred genes include, e.g., thioredoxin, staphnuclease, lac repressor, gal4 or an antibody.

By recombinant vector is meant a vector having a nucleic acid sequence which is not normally present in the vector. The nucleic acid sequence is inserted into a gene present on the vector. Insertion of a nucleic acid into a gene is meant to include insertion within the gene or immediately 5' or 3' to, respectively, the beginning or end of the gene, such that when expressed, a fusion gene product is made. The nucleic acid sequence that is inserted includes, e.g., a synthesized nucleic acid sequence or a fragment of another nucleic acid molecule. The nucleic acid sequence encodes a displayed peptide sequence. By displayed peptide sequence is meant a peptide sequence that is on the surface of, e.g., a virion, e.g. a phage or virus, a cell, a spore, or an expressed gene product. It is preferable to have the displayed peptide displayed such that it is able to bind to added target molecules. A displayed peptide sequence can be identical to, or not identical to, a naturally occurring peptide sequence.

The displayed peptide sequence can vary in size. As the size increases, the complexity of the anchor library increases, such that at some point a complete library is not obtainable. Complete libraries or incomplete libraries can be used in this invention. In certain embodiments, the complexity of the anchor library is at least about $10^8$ to about $10^{11}$. Preferably, the complexity is at least about $10^9$. It is preferred that the total size of the displayed peptide sequence (the random amino acids plus the spacer amino acids) should not be greater than about 100 amino acids long, more preferably not greater than about 50 amino acids long, and most preferably not greater than about 25 amino acids long. A particularly preferred library is made up of displayed peptides in which the longest of the peptides is 16 amino acids, i.e., a 16 mer library.

In large standard libraries, e.g., of 16 mers or greater, it is ordinarily not possible to search a library which contains all possible combinations of the 16 random amino acids. A major advantage of the anchor libraries of this invention is that these large libraries can be searched by looking for a reduced number of essential amino acid contacts between the peptides and the target. Preferably, the number of essential amino acid contacts should be sufficient to achieve micromolar binding. Preferably, the reduced number of essential contacts is about three to about ten, and most preferably it is about four. See Example 4. Thus, e.g., the number of combinations of four amino acid residue contacts in a 16 mer library is much less than the total number of combinations of all 16 amino acids in a 16 mer library, and therefore, this invention makes it possible to determine four important contact amino acids in a peptide of 16 amino acids in length, as opposed to standard screening of standard libraries in which such determinations cannot ordinarily be made.

In one embodiment of the invention, the displayed peptide sequence comprises

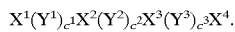

$X^1, X^2, X^3$ and $X^4$ are amino acid residues, each of which can be the same or different from any one of the others. Preferably, the amino acids are chosen from the 20 amino acids commonly found in naturally occurring proteins.

$Y^1, Y^2$ and $Y^3$ can be any specified amino acid residue or combination of specified amino acid residues, and each of the Ys, if present, can be the same or different from any one of the others. Preferably, the amino acids are spacer amino acids which will not significantly interfere with the binding between the peptide sequence and a target molecule. It is preferable to use combinations of two or more amino acids for the Y amino acids in a given library so as to reduce any limitations in the conformations of the displayed peptide that might be imposed by use of only one given amino acid. Most preferably, glycine and alanine residues are used in combination in the library. Glycine and alanine are small side chain amino acids that appear to act more as blanks than interfering contacts. In other embodiments, the Y amino acids can be amino acids which are chosen because they do significantly affect in some way the binding between the peptide sequence and a target molecule. For example, glycine and cysteine residues can be used in combination, or alanine and cysteine residues can be used in combination.

$Y^1, Y^2$ and $Y^3$, are, respectively $c^1, c^2$ and $c^3$ amino acid residues long. $c^1, c^2$ and $c^3$ can be the same or different from any one of the others. Preferably, each of $c^1, c^2$ and $c^3$ is 0 to about 20, more preferably is 0 to about 10, even more preferably is 0 to about 6, and most preferably is 0 to about 4.

For example, in an anchor library where each of the c's are 0 to 4, and the Y's are a combination of glycine and alanine, the minimal structure of the peptide sequence is 4 amino acids long (where each of $c^1, c^2$ and $c^3$ is 0):

and the maximal structure of the peptide sequence is 16 amino acids long (where each of $c^1, c^2$ and $c^3$ is 4):

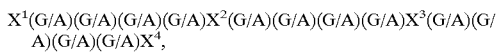

where (G/A) is a glycine or alanine residue. This anchor library also contains all other in-between permutations of c, e.g., where $c^1$ is 0, $c^2$ is 1 and $c^3$ is 1; where $c^1$ is 1, $c^2$ is 1 and $c^3$ is 1; where $c^1$ is 2, $c^2$ is 1 and $c^3$ is 1; etc. All possible permutations of alanine and glycine for each of the designated c values are also included in this anchor library.

It is preferred that all possible permutations of the displayed sequence are present, that is, all combinations of c values and all combinations of, e.g., alanine and/or glycine, for each of the c values. In other embodiments, at least about $10^5$ to about $10^8$ permutations of all possible permutations are present in the anchor library, or at least about $10^4$ permutations of all possible permutations are present in the anchor library, or at least about $10^5$ permutations of all possible permutations are present in the anchor library, or at least about $10^6$ permutations of all possible permutations are present in the anchor library, or at least about $10^7$ permutations of all possible permutations are present in the anchor library, or at least about $10^8$ permutations of all possible permutations are present in the anchor library, or at least about $10^9$ permutations of all possible permutations are present in the anchor library.

In certain embodiments, the library does not contain more than about 10% of displayed peptide sequences different from the first mentioned displayed peptide sequences. In other embodiments, the library does not contain more than about 1% of displayed peptide sequences different from the first mentioned displayed peptide sequences. And in yet other embodiments, the library does not contain more than about 0.1% of displayed peptide sequences different from the first mentioned displayed peptide sequences.

In certain embodiments of the invention, the displayed peptide can have additional units of $X(Y)_c$. For example, it can have preferably about 1 to about 10 additional units, more preferably about 1 to about 5 additional units, and most preferably about 1 to about 3 additional units. In other embodiments, one or more additional units of X alone or $(Y)_c$ alone can be present.

In yet other embodiments of the invention, the anchor libraries described above can have at least one core binding sequence, denoted by B, of p amino acid residues in length. B can be any size, e.g., from a single amino acid to the size of a gene. Preferably, p is about 1 to about 20, more preferably p is about 4 to about 10, and most preferably p is about 6. By core binding sequence is meant a peptide sequence which is known to bind to a target molecule. In certain embodiments, the core binding sequence is additional to the amino acid residues of the displayed peptide sequences described above. In such libraries, the core binding sequence can be positioned on the $NH_2$-terminal or COOH-terminal side of any of the $X^1$, $X^2$, $X^3$ or $X^4$ amino acid residues, or on the $NH_2$-terminal or COOH-terminal side of any of the Y, e.g., alanine or glycine, residues. In other embodiments, at least one of the X residues is replaced with the core binding sequence. In yet other embodiments, at least one of the Y residues, e.g., one of the alanine or glycine residues, is replaced with a core binding sequence. Inclusion of a known core binding sequence in the anchor library allows identification of surrounding amino acid residues which are additional important contacts between the peptide and the target molecule. The invention thus allows identification of better binding sequences by identifying additional amino acids surrounding the core binding sequence which in combination with the known core binding sequence exhibit enhanced binding as compared to the known core binding sequence alone.

In certain embodiments, more than one known binding sequence is present in each of the displayed peptide sequences of the anchor library. These multiple known binding sequences can be adjacent to, or not adjacent to, each other, and can be identical to, or not identical to, each other.

In certain embodiments, the anchor libraries have at least one constraint imposed upon the displayed peptide sequence. A constraint includes, e.g., a crosslink, a stacking interaction, a positive or negative charge, hydrophobicity, hydrophilicity, a structural motif and combinations thereof. In certain embodiments, more than one constraint is present in each of the displayed peptide sequences of the anchor library. These multiple constraints can be adjacent to, or not adjacent to, each other, and can be identical to, or not identical to, each other.

A crosslink includes, e.g., a disulfide bond. In certain embodiments, the displayed peptide has at least one cysteine residue. The cysteine residue can be, e.g., additional to the amino acid residues of the displayed peptide sequences described above. In such libraries, the cysteine residue can be positioned on the $NH_2$-terminal or COOH-terminal side of any of the $X^1$, $X^2$, $X^3$ or $X^4$ amino acid residues, or on the $NH_2$-terminal or COOH-terminal side of any of the Y, e.g., alanine or glycine, residues. In other embodiments, at least one of the X residues is a cysteine residue. In yet other embodiments, at least one of the Y residues, e.g., one of the alanine or glycine residues, is replaced with a cysteine residue. Multiple cysteines can be present in each of the peptides so as to form potential disulfide bonds within a random series. Disulfide bonds can be formed within the displayed peptide sequence itself or between the displayed peptide sequence and the target molecule.

A structural motif includes, e.g., a zinc finger formation, a leucine zipper, and a R-turn structure in the peptide. The sequences asp gly or pro gly are likely to induce β-turns, either alone or in combination with, e.g., a disulfide bond.

In other embodiments, the anchor libraries can be constructed to have both a core binding sequence and a constraint, e.g., at least one cysteine residue. In one such embodiment, at least one of the X residues can be, e.g., either a cysteine or a glycine such that the displayed peptide sequence is:

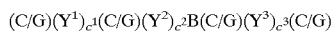

where (C/G) is a cysteine or glycine residue. In such a library, multiple cysteines are present so as to form potential disulfide bonds within a random series.

In yet other embodiments, the displayed peptide sequence comprises:

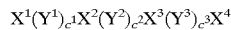

wherein each $Y^1$, $Y^2$ and $Y^3$ is alanine or glycine or a core binding sequence B of p amino acid residues in length or a combination of alanine and glycine or alanine and B or glycine and B.

And in yet other embodiments, the displayed peptide sequence comprises:

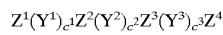

wherein each $Z^1$, $Z^2$, $Z^3$ and $Z^4$ is an amino acid residue or a core binding sequence B of p amino acid residues in length and any of $Z^1$, $Z^2$, $Z^3$ and $Z^4$ can be the same or different from any one other, and wherein $Z^1$ and $Z^4$ are each attached to an amino acid residue that flanks the displayed peptide sequence.

Other embodiments include anchor libraries constructed with other configurations of combinations between X residues and/or Y residues and/or B sequences and/or cysteine residues and/or other constraints, as is obvious to those skilled in the art.

The invention also includes a method of making the anchor libraries described above. A collection of nucleic acid sequences is synthesized and inserted into vectors to give recombinant vectors. These recombinant vectors are introduced into a host. The host having the recombinant vectors is propagated so as to result in a collection of recombinant vectors, each of the recombinant vectors having a nucleic acid sequence from the collection of nucleic acid sequences which encodes a displayed peptide sequence. The peptide sequence is any of the peptide sequences discussed above, e.g., $X^1(Y^1)_{c1}X^2(Y^2)_{c2}X^3(Y^3)_{c3}X^4$, with or without at least one core binding sequence, and with or without at least one constraint, e.g., a cysteine residue. In certain embodiments, at least about $10^5$ to about $10^8$ permutations, or about $10^4$ permutations, or about $10^5$ permutations, or about $10^6$ permutations, or about $10^7$ permutations, or about $10^8$ permutations, or about $10^9$ permutations, of all possible permutations of the displayed peptide sequence are present in the anchor library. In other embodiments, the library does not contain more than about 10%, or more than about 1%, or more than about 0.1%, of displayed peptide sequences different from the first mentioned displayed peptide sequences.

The nucleic acids that encode the anchor library can be obtained by any method which produces the requisite permuted nucleic acids. For example, a split synthesis procedure can be used. See, e.g., Cormack and Struhl, Science 262:244–248 (1993). Examples 1 and 3 describe examples of using split synthesis to make nucleic acid inserts for anchor libraries.

The invention further includes a method of using the anchor libraries described above to identify a peptide sequence that binds to a target. An anchor library having a collection of recombinant vectors, each of which has a nucleic acid sequence which encodes a displayed peptide sequence, is provided. The displayed peptide sequence can be any of the peptide sequences discussed above, e.g., $X^1(Y^1)_{c1}X^2(Y^2)_{c2}X^3(Y^3)_{c3}X^4$, with or without at least one core binding sequence, and with or without at least one constraint, e.g., a cysteine residue. Expression and display of the peptide sequence is permitted. The anchor library is contacted with the target under conditions in which the displayed peptide sequence binds to the target, and the displayed peptide sequence which binds to the target is identified.

Target is meant to include any molecule with which the displayed peptide sequence will bind. Targets include, e.g., proteinaceous and non-proteinaceous molecules. Examples of targets are ligands, receptors, hormones, cytokines, antibodies, antigens, enzymes, enzyme substrates and viruses. In some cases, the binding peptide modulates the original activity of the target molecule, and therefore can be useful as a drug. The target includes, e.g., drug antagonists and agonists. The binding peptides can be used, e.g., for diagnostic or therapeutic applications.

The contacting step can be done by any method in which the displayed peptide sequence will bind, directly or indirectly, to the target. These methods include, e.g., screens and selections. Preferably, an affinity purification method is used. Affinity purification includes, e.g., biopanning. For example, a phage anchor library having displayed peptide sequences is mixed with biotinylated target, resulting in phage:biotinylated target complex if a displayed peptide sequence binds to the target. The mixture is added to a streptavidin coated substance, e.g., beads or a petri plate. The resulting biotin-streptavidin bond allows isolation of the phage carrying peptide sequences that bind to the target., It is preferable to do multiple rounds of biopanning to reduce background. See Example 2.

Identification of the displayed peptide sequence includes, e.g., determining the sequence of amino acids that comprise the peptide. Identification can be accomplished, e.g., by amplifying the recombinant vector which has the nucleic acid sequence which encodes for the displayed peptide sequence which binds to the target, and sequencing the nucleic acid sequence by standard procedures known in the art to determine the displayed peptide sequence which binds to the target. If desired, the peptide thus identified can be synthesized using standard procedures known in the art and further tested for its ability to bind to the target in vitro and/or in cell-based, and/or animal models. See Example 2.

In a given anchor library, the ability to determine essential amino acid contacts between the displayed peptide and a target molecule is aided by the ability to observe conserved amino acid residues in the different displayed peptides which are able to bind to the target. Conserved amino acid residues are meant to include different DNA codons for the same amino acid or different DNA codons for functionally similar amino acids. The consensus is determined by comparing the sequence of the individual clones obtained from a library screen. It is preferable that the library have sufficient complexity in order to observe such a consensus.

Also included in the invention is a peptide identified by use of any of the anchor libraries described above in which the peptide is useful as a diagnostic or therapeutic product in that the peptide is able to bind to a target molecule which is involved in a physiological process. For example, the target molecule can be a receptor involved in inflammation, e.g., IL-1, or in prostate cancer, e.g., GnRH; or the target molecule can be an enzyme, e.g., a protease, e.g., HIV protease. By binding to these or other target molecules that are involved in various abnormal conditions or diseases, the binding peptides of this invention modulate the original activity of the target molecule and are therefore useful as diagnostic or therapeutic products.

The invention also includes a library which has a collection of nucleic acid molecules encoding peptides having random amino acids, the improvement comprising a library in which the random amino acids are not continuous so that the amino acids in the peptide that are important contacts for interaction between the peptide and a target molecule can be identified.

The invention also includes a library having a collection of nucleic acid molecules encoding peptides having random amino acids, the improvement comprising nucleic acid molecules encoding alanine or glycine or a combination of alanine and glycine residues in varying numbers acting as spacers between the random amino acids so that amino acid residues in a peptide that are important contacts for interaction between the peptide and a target molecule can be identified.

The invention further provides a collection of recombinant DNA molecules encoding peptide sequences having a plurality of different binding domains. The peptide sequences comprise: $X^1(Y^1)_{c^1}X^2(Y^2)_{c^2}X^3(Y^3)_{c^3}X^4$, wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively $c^1$, $c^2$ and $c^3$ amino acid residues long and any of $Y^1$, $Y^2$ and $Y^3$ if present can be the same or different from any one other, wherein each of $c^1$, $c^2$ and $c^3$ is 0 to about 20, wherein $X^1$ and $X^4$ are each attached to an amino acid residue that flanks the peptide sequence, and wherein at least about $10^5$ to about $10^8$ permutations, or about $10^4$ permutations, or about $10^5$ permutations, or about $10^6$ permutations, or about $10^7$ permutations, or about $10^8$ permutations, or about $10^9$ permutations, of all possible permutations of the peptide sequence are present in the collection. In other embodiments, the collection does not contain more than about 10%, or more than about 1%, or more than about 0.1%, of displayed peptide sequences different from the first mentioned displayed peptide sequences. In certain embodiments, the peptide sequences are displayed on the surface of a biological material, e.g., a virus, phage, cell, spore or gene product.

The invention also includes a recombinant filamentous phage having a displayed peptide sequence with known binding properties. The displayed peptide sequence is foreign to the filamentous phage. The displayed peptide sequence comprises: $X^1(Y^1)_{c^1}X^2(Y^2)_{c^2}X^3(Y^3)_{c^3}X^4$, wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively $c^1$, $c^2$ and $c^3$ amino acid residues long and any of $Y^1$, $Y^2$ and $Y^3$ if present can be the same or different from any one other, wherein each of $c^1$, $c^2$ and $c^3$ is 0 to about 20, wherein $X^1$ and $X^4$ are each attached to an amino acid residue that flanks the displayed peptide sequence, and wherein the displayed peptide sequence is able to bind to a target. In certain embodiments, at least one of $Y^1$, $Y^2$ and $Y^3$ is at least about 20 amino acid residues long, preferably is at least about 10 amino acid residues long, more preferably is at least about 6 amino acid residues long, even more preferably is at least about 4 amino acid residues long, more preferably yet is at least about 3 amino acid residues long, more preferably yet is at least about 2 amino acid residues long, and most preferably is at least about 1 amino acid residue long.

The invention also includes a recombinant vector having a nucleic acid sequence inserted in a gene. The nucleic acid sequence encodes a displayed peptide sequence having known binding properties. The displayed peptide sequence comprises: $X^1(Y^1)_{c^1}X^2(Y^2)_{c^2}X^3(Y^3)_{c^3}X^4$, wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively $c^1$, $c^2$ and $c^3$ amino acid residues long and any of $Y^1$, $Y^2$ and $Y^3$ if present can be the same or different from any one other, wherein each of $c^1$, $c^2$ and $c^3$ is 0 to about 20, wherein $X^1$ and $X^4$ are each attached to an amino acid residue that flanks the displayed peptide sequence, and wherein the displayed peptide sequence is able to bind to a target. In certain embodiments, at least one of $Y^1$, $Y^2$ and $Y^3$ is at least about 20 amino acid residues long, preferably is at least about 10 amino acid residues long, more preferably is at least about 6 amino acid residues long, even more preferably is at least about 4 amino acid residues long, more preferably yet is at least about 3 amino acid residues long, more preferably yet is at least about 2 amino acid residues long, and most preferably is at least about 1 amino acid residue long.

The invention also includes a recombinant nucleic acid molecule having a nucleic acid sequence inserted in a gene. The nucleic acid sequence encodes a displayed peptide sequence having known binding properties. The displayed peptide sequence comprises: $X^1(Y^1)_{c^1}X^2(Y^2)_{c^2}X^3(Y^3)_{c^3}X^4$, wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively $c^1$, $c^2$ and $c^3$ amino acid residues long and any of $Y^1$, $Y^2$ and $Y^3$ if present can be the same or different from any one other, wherein each of $c^1$, $c^2$ and $c^3$ is 0 to about 20, wherein $X^1$ and $X^4$ are each attached to an amino acid residue that flanks the displayed peptide sequence, and wherein the displayed peptide sequence is able to bind to a target. In certain embodiments, at least one of $Y^1$, $Y^2$ and $Y^3$ is at least about 20 amino acid residues long, preferably is at least about 10 amino acid residues long, more preferably is at least about 6 amino acid residues long, more preferably is at least about 4 amino acid residues long, more preferably yet is at least about 3 amino acid residues long, more preferably yet is at least about 2 amino acid residues long, and most preferably is at least about 1 amino acid residue long.

The invention further includes a recombinant protein having a displayed peptide sequence having known binding properties. The displayed peptide sequence comprises: $X^1(Y^1)_{c^1}X^2(Y^2)_{c^2}X^3(Y^3)_{c^3}X^4$, wherein each $X^1$, $X^2$, $X^3$ and $X^4$ is an amino acid residue and any of $X^1$, $X^2$, $X^3$ and $X^4$ can be the same or different from any one other, wherein each $Y^1$, $Y^2$ and $Y^3$ is alanine or glycine or a combination of alanine and glycine that is respectively $c^1$, $c^2$ and $c^3$ amino acid residues long and any of $Y^1$, $Y^2$ and $Y^3$ if present can be the same or different from any one other, wherein each of $c^1$, $c^2$ and $c^3$ is 0 to about 20, wherein $X^1$ and $X^4$ are each attached to an amino acid residue that flanks the displayed peptide sequence, and wherein the displayed peptide sequence is able to bind to a target. In certain embodiments, at least one of $Y^1$, $Y^2$ and $Y^3$ is at least about 20 amino acid residues long, preferably is at least about 10 amino acid residues long, more preferably is at least about 6 amino acid residues long, even more preferably is at least about 4 amino acid residues long, more preferably yet is at least about 3 amino acid residues long, more preferably yet is at least about 2 amino acid residues long, and most preferably is at least about 1 amino acid residue long.

EXAMPLES

Example 1

Construction of a Phage Anchor Library

This example illustrates the construction of a phage anchor library having random amino acid codons distributed throughout a domain of alanine and/or glycine codons. Standard cloning techniques known to those skilled in the art were used.

(a) Vector Preparation

30 μg of Fuse5 (Smith and Scott, Methods in Enzymology 217:228–257 (1993)) was cleaved with 200 units of endonuclease Sfi I in 500 μl of NEB #2 restriction buffer for 10 hours. The reaction was terminated with addition of 15 mM EDTA, followed by phenol and chloroform extractions. The DNA was recovered by isopropanol precipitation, resuspended in 500 μl of TE, and recovered by EtOH precipitation.

(b) Insert Preparations

The anchor insert used in the library was synthesized as a single stranded oligomer using split synthesis. See. e.g., Cormack and Struhl, Science 262:244–248 (1993). This process creates combinations of sequences which differ from each other.

Using split synthesis, five templates were synthesized and mixed three times to produce the anchor library:

| | | |
|---|---|---|
| 1) | GGGCTGCCGGGNNKNNK | COMBINE AND |
| | (Seq. ID No. 1) | SPLIT |
| 2) | GGCTGCCGGGNNKGSNNNK | |
| | (Seq. ID No. 2) | |
| 3) | GGGCTGCCGGGNNKGSNGSNNNK | |
| | (Seq. ID No. 3) | |
| 4) | GGGCTGCCGGGNNKGSNGSNGSNNNK | |
| | (Seq. ID No. 4) | |
| 5) | GGGCTGCCGGGNNKGSNGSNGSNGSNNNK | |
| | (Seq. ID No. 5) | |
| 6) | NNK | COMBINE AND |
| 7) | GSNNNK | SPLIT |
| 8) | GSNGSNNNK | |
| 9) | GSNGSNGSNNNK | |
| | (Seq. ID No. 6) | |
| 10) | GSNGSNGSNGSNNNK | |
| | (Seq. ID No. 7) | |
| 11) | NNKGGTGGTGCTGCTG | COMBINE |
| | (Seq. ID No. 8) | |
| 12) | GSNNNKGGTGGTGCTGCTG | |
| | (Seq. ID No. 9) | |
| 13) | GSNGSNNNKGGTGGTGCTGCTG | |
| | (Seq. ID No. 10) | |
| 14) | GSNGSNGSNNNKGGTGGTGCTGCTG | |
| | (Seq. ID No. 11) | |
| 15) | GSNGSNGSNGSNNNKGGTGGTGCTGCTG | |
| | (Seq. ID No. 12) | |

N = equal mix of G, A, T, C
S = equal mix of G, C
K = equal mix of G, T

DNA was chemically synthesized such that column 1 contained the DNA sequence GGGCTGCCGGG (Seq. ID No. 13), followed by DNA encoding a random amino acid, NNK, followed by DNA encoding a second random amino acid, NNK. Column 2 encoded the DNA sequence GGGCTGCCGGG (Seq. ID No. 13), followed by a random amino acid codon, NNK, followed by either a glycine or alanine codon, GSN, and then followed by a random amino acid codon, NNK. Columns 3, 4 and 5 encoded the DNA sequence GGGCTGCCGGG (Seq. ID No. 13), followed by a random amino acid codon, NNK, followed by, respectively, 2, 3 and 4 glycine and/or alanine codons, GSN, and then followed by a random amino acid codon, NNK.

After synthesis of columns 1–5, the resins from the five columns were mixed, resulting in a pool of oligomers which contained two random amino acids separated by 0 to 4 glycine and/or alanine residues. This entire mixture was then split into 5 new columns, denoted 6–10. Each of these columns was subjected to further DNA synthesis, resulting in, respectively, codons for 0, 1, 2, 3 and 4 glycine and/or alanine residues, GSN, followed by a random amino acid, NNK. Because the additions of columns 6–10 were conducted on a mixture of resins from columns 1–5, the mixture of columns 6–10 resulted in oligomers that all have three random amino acids, such that the neighboring random amino acids are separated by 0 to 4 glycine and/or alanine residues.

One additional round of split synthesis was undertaken in which the mixtures of columns 6–10 were extended with 0 to 4 glycine and/or alanine residues, GSN, and one more additional random amino acid, NNK, followed by the sequence GGTGGTGCTGCTG (Seq. ID No. 14). The final mixture of these columns resulted in a series of oligomers with four random amino acids such that the neighboring random amino acids are separated by 0 to 4 glycine and/or alanine residues.

Two additional oligomers, pins, CCCGGCAGCCCCGT (Seq. ID No. 15) and CAGCACCACC (Seq. ID No. 16), were synthesized which hybridize to the anchor oligomers so as to reconstruct double stranded DNA near the termini of the insert with three single strand nucleotide overhangs corresponding to Sfi I overhangs.

The insert and pin oligomers were kinased at 10 $\mu$g/30 $\mu$l kinase buffer from NEB with 1 mM ATP at 37° C. for 30 minutes, followed by inactivation at 68° C. for 5 minutes. The anchor oligomer was annealed to the pin oligomers in 500 mM NaCl, 50 mM Tris pH 7.5 at 68° C. for 10 minutes and cooled to room temperature over 30 minutes. Each of the oligomers was at 5 $\mu$M during the annealing.

It is noted that similar results can be obtained with other 5' and 3' flanking sequences on the anchor inserts, and with other corresponding pin sequences altered appropriately, as can be chosen by those skilled in the art. Moreover, other restriction sites can be used as appropriate for any given vector, as is known to those skilled in the art.

(c) Vector Ligation

30 $\mu$g of DNA vector was ligated to assembled insert at 5 $\mu$g/ml vector and three-fold excess assembled insert in NEB ligation buffer with 100 units of T4 DNA ligase at 10° C. for 16 hours. DNA was purified from ligation buffer by phenol and chloroform extractions, followed by EtOH precipitation and resuspension in TE.

(d) DNA Transformation

DNA was transformed into MC1061 (Wertman et al., Gene 49:253–262 (1986)) electrocompetent cells using 0.5 $\mu$g of DNA per 100 $\mu$l of cells using 0.2 cm electroporator cells and a BioRad electroporator set at 25 $\mu$F, 2.5 KV and 200 ohms. Shocked cells were recovered in SOC media, grown out at 37° C. for 20 minutes and inoculated into LB containing 20 $\mu$g/ml tetracycline.

(e) Library Phage Isolation

Phage released from transformed cells were isolated after growing for 16 hours. Phage were separated from cells by centrifugation at 4° C. at 4.2K for 30 min. In a Beckman J6, followed by a second centrifugation of the supernatant at 4.2K for 30 min. Phage were precipitated with the addition of 150 ml at 16.7% PEG/3.3 M NaCl per liter of supernatant. Mixed solutions were incubated at 4° C. for 16 hours. Precipitated phage was collected at 4.2K in a J6 followed by resuspension in 40 ml of TBS. Resuspended phage were precipitated again with the addition of 4.5 ml of PEG solution for 4 hours. Phage were collected at 5K in a Beckman JA20 at 4° C. Phage were suspended in 7 ml of TBS and brought to 1.3 mg/ml density by the addition of 1 gm of CsCl per 2.226 gm of aqueous solution. Phage were subjected to equilibrium centrifugation in a type 80 rotor at 45K rpm for 40 hours. Phage bands were isolated, diluted 20 fold with TBS and pelleted at 40 K in a Type 50 rotor. Pellets were resuspended in 0.7 ml of TBS and used as is for biopanning at approximately $3\times10^{13}$ phage/ml.

Example 2

Biopanning to Select for Peptide Binding Sequences

This example illustrates biopanning of the phage library obtained from Example 1 to select for displayed peptide sequences that bind to biotinylated IL-1B. The phage act as affinity-selectable vectors in that the displayed peptide binds specifically to immobilized IL-1B if the library contains a displayed peptide that can so interact with IL-1B.

(a) Binding

Biotinylated IL-1 (b-IL-1) (Yew et al., JBC 264(30):17691–17697 (1989)) is incubated with $1\times10^{11}$ phage in 20 $\mu$l of TBS for 20 minutes at 22° C. The phage:(b-IL-1) complex is isolated from free phage by addition of streptavadin coated paramagnetic beads for an additional 10 minutes. Magnetic beads are collected by attraction with a magnet and washed with TBS containing 0.5% Tween-20 for a total of 7 washes over 30 minutes. The remaining phage that are bound to the beads (by way of b-IL-1 binding to streptavadin) are recovered by elution with 100 $\mu$l of 100 mM glycine pH 2.2 for 10 minutes. Eluted phage are neutralized with 1 M Tris base.

(b) Amplification

Eluted phage are amplified by infection into log phase K91 *E. coli* (Lyons and Zinder, Virology 49:45–60 (1972); Smith and Scott, Methods in Enzymology 217:228–257 (1993)) at an moi of 0.0001. Approximately $10^5$ phage are amplified by plating on 10 LB agar petri dishes containing 20 $\mu$g/ml tetracycline. The phage released from infected cells, approximately $10^{12}$ phage, are harvested by washing the LB agar plates with LB, and purified as above through the two PEG precipitations and resuspended at $10^{13}$ phage/ml.

Amplified phage are further subjected to two additional rounds of biopanning using the binding and amplification conditions described above.

(c) Sequencing Inserts

After three rounds of biopanning, individual phage are isolated and sequenced to reveal the DNA sequence that encodes for the displayed peptide in the selected phage. Sequencing is done according to manufacturer's protocol for Sequenase 2.0 (United States Biochemical, Cleveland, Ohio 44122).

(d) Peptide Synthesis

Peptides representing affinity purified phage are synthesized (Research Genetics, Huntsville, Ala. 35801) and tested for their ability to bind IL-1 and effect IL-1 binding to IL-1 receptor in cell based and animal models. Slack et al., Biotechniques 10:1132–1138 (1989).

Example 3

Construction of a Phage Anchor Library Having Codons for a Known Core Peptide Binding Sequence This example illustrates construction of a phage anchor library which has codons for a known core peptide binding sequence which binds to a target molecule, surrounded by random amino acid codons distributed throughout a domain of random alanine and/or glycine codons. Construction of this type of library is similar to that described in Example 1, except that the oligomer constructs not only have the random amino acid codons and glycine and/or alanine codons, but also have nucleic acid sequences which code for a known core peptide binding sequence, denoted as B:

| | | |
|---|---|---|
| 1) | GGGCTGCCGGGNNKNNK (Seq ID No. 1) | COMBINE AND SPLIT |
| 2) | GGGCTGCCGGGNNKGNNNK (Seq. ID No. 2) | |
| 3) | GGGCTGCCGGGNNKGSNGSNNNK (Seq. ID No. 3) | |
| 4) | GGGCTGCCGGGNNKGSNGSNGSNNNK (Seq. ID No. 4) | |
| 5) | GGGCTGCCGGGNNKGSNGSNGSNGSNNNK (Seq. ID No. 5) | |
| 6) | BNNK | COMBINE AND SPLIT |
| 7) | BGSNNNK | |
| 8) | BGSNGSNNNK | |
| 9) | BGSNGSNGSNNNK (Seq. ID No. 6) | |
| 10) | BGSNGSNGSNGSNNNK (Seq. ID No. 7) | |
| 11) | NNKGGTGGTGCTGCTG (Seq. ID No. 8) | COMBINE |
| 12) | GSNNNKGGTGGTGCTGCTG (Seq. ID No. 9) | |
| 13) | GSNGSNNNKGGTGGTGCTGCTG (Seq. ID No. 10) | |
| 14) | GSNGSNGSNNNKGGTGGTGCTGCTG (Seq. ID No. 11) | |
| 15) | GSNGSNGSNGSNNNKGGTGGTGCTGCTG (Seq. ID No. 12) | |

The anchor library can also be constructed such that sequence B is located, e.g., before or after any of the other NNK or GSN codons.

Other anchor libraries, containing additions or substitutions of nucleic acid sequences, can be constructed using similar methods. For example, codons for cysteine, or any other specified amino acid or sequence of amino acids, can be substituted for the nucleic acid sequence coding for the core binding sequence B in the above-described split synthesis. Anchor libraries containing two or more core binding sequences, cysteines, or any other specified amino acid or sequence of amino acids, also can be constructed using similar procedures as described, except that the multiple additions are synthesized as part of the oligomers at multiple positions, e.g., each can be located before or after any of the NNK or GSN codons, as can be chosen by one skilled in the art.

Example 4

Four Amino Acid Residues in a Peptide is Sufficient for Binding to a Target

This example illustrates that four amino acid residues in a peptide are sufficient for micromolar binding between the peptide and its target.

A hexamer phage library was constructed essentially as described for the anchor libraries, except the oligonucleotide was: GGGCTGCCGGGNNKNNKNNKNNKNNKGGTGGTGCTGCTG (Seq. ID No. 18). The library was screened against an antibody to hCG by biopanning as described in Example 2. The phage that bound to the antibody contained the consensus sequence XaaThrProTrpXaaGln (Seq. ID No. 17), where X was not absolutely specified. Peptides were synthesized which corresponded to the identified sequences and the flanking amino acids found in the phage. These peptides had an IC50 of 4.5 μM compared to 10 nM for hCG. IC50 is equal to the concentration of peptide necessary to prevent 50% of hCG-I$^{125}$ from binding to the antibody. Therefore, four amino acid residues were sufficient to result in μM binding.

Those skilled in the art will be able to ascertain, using no more than routine experimentation, many equivalents of the specific embodiments of the invention described herein. These and all other equivalents are intended to be encompassed by the following claims.

What is claimed is:

1. An anchor library, consisting essentially of:
a collection of recombinant vectors,
each of said recombinant vectors having a nucleic acid sequence inserted in a gene, said nucleic acid sequence encoding a displayed peptide sequence,
said displayed peptide sequence of each of said vectors comprising $$X^1(Y^1)_{c1}X^2(Y^2)_{c2}X^3(Y^3)_{c3}X^4$$

wherein
each $X^1$, $X^2$, $X^3$, and $X^4$ is an amino acid residue and any of $X^1$, $X^2$, $X^3$, and $X^4$ can be the same or different from each other, wherein each $Y^1$, $Y^2$ and $Y^3$ is alanine or glycine or a combination of alanine and glycine that is respectively $c^1$, $c^2$ and $c3$ amino acid residues long and any of $Y^1$, $Y^2$ and $Y^3$ can be the same or different from each other, wherein $c^1$, $c^2$ and $c^3$ are 1–20, provided that at least one of $c^1$, $c^2$ and $c^3$ is 3 to 20, and
wherein at least about $10^5$ distinct displayed peptide sequences are encoded by said anchor library.

2. The library of claim 1 wherein at least about $10^9$ displayed peptide sequences are present in said anchor library.

3. The library of claim 1 wherein at least about $10^6$ displayed peptide sequences are present in said anchor library.

4. The library of claim 1 wherein at least about $10^7$ displayed peptide sequences are present in said anchor library.

5. The library of claim 1 wherein at least about $10^8$ displayed peptide sequences are present in said anchor library.

6. The library of claim 1 wherein said vector is selected from the group consisting of a virus, phage, plasmid and cosmid.

7. The library of claim 1 wherein said vector is a filamentous phage.

8. The library of claim 7 wherein said gene that said nucleic acid sequence is inserted in is a coat protein gene of said filamentous phage.

9. The library of claim 7 wherein said gene that said nucleic acid sequence is inserted in is a filamentous phage gene selected from the group consisting of gene III and gene VIII.

10. The library of claim 7 wherein said gene that said nucleic acid sequence is inserted in is selected from the group consisting of thioredoxin, staphnuclease, lac repressor, gal4 and an antibody.

11. The library of claim 1 wherein said displayed peptide sequence is displayed on the surface of a virion.

12. The library of claim 1 wherein said displayed peptide sequence is displayed on the surface of a cell.

13. The library of claim 1 wherein said displayed peptide sequence is displayed on the surface of an expressed gene product.

14. The library of claim 1 wherein at least one of said $c^1$, $c^2$ and $c^3$ is at least 4.

15. The library of claim 1 wherein at least one of said $c^1$, $c^2$ and $c^3$ is at least 6.

16. The library of claim 1 wherein at least one of said $c^1$, $c^2$ and $c^3$ is at least 10.

17. The library of claim 1 further comprising about 1 to about 10 additional units of $X(Y)_c$.

18. The library of claim 1 wherein said displayed peptide sequence is not identical to a naturally occurring peptide sequence.

19. The library of claim 1 wherein said displayed peptide sequence is identical to a naturally occurring peptide sequence.

20. The library of claim 1 wherein said displayed peptide sequence further comprises at least one B, said B being a core binding sequence of 1 to 20 amino acid residues in length.

21. The library of claim 20 wherein said B is 4 to 10 amino acid residues in length.

22. The library of claim 20 wherein said B is 6 amino acid residues in length.

23. The library of claim 20 wherein said B is selected from the group consisting of said B being on the $NH_2$-terminal side of any of said $X^1$, $X^2$, $X^3$ or $X^4$ amino acid residues, said B being on the COOH-terminal side of any of said $X^1$, $X^2$, $X^3$ or $X^4$ amino acid residues, said B being on the $NH_2$-terminal side of any of said alanine or glycine residues, and said B being on the COOH-terminal side of any of said alanine or glycine residues.

24. The library of claim 20 wherein more than one said B is present.

25. The library of claim 24 wherein said Bs are adjacent to each other.

26. The library of claim 24 wherein said Bs are not adjacent to each other.

27. The library of claim 24 wherein said Bs are identical to each other.

28. The library of claim 24 wherein said Bs are not identical to each other.

29. The library of claim 1 wherein said displayed peptide sequence further comprises at least one constraint selected from the group consisting of a crosslink, a stacking interaction, a positive or negative charge, hydrophobicity, hydrophilicity, a structural motif and combinations thereof.

30. The library of claim 29 wherein said crosslink is a disulfide bond.

31. The library of claim 1 wherein said displayed peptide sequence further comprises at least one cysteine residue.

32. The library of claim 31 wherein said cysteine residue is selected from the group consisting of said cysteine residue being on the $NH_2$-terminal side of any of said $X^1$, $X^2$, $X^3$ or $X^4$ amino acid residues, said cysteine residue being on the COOH-terminal side of any of said $X^1$, $X^2$, $X^3$ or $X^4$ amino acid residues, said cysteine residue being on the $NH_2$-terminal side of any of said alanine or glycine residues, and said cysteine residue being on the COOH-terminal side of any of said alanine or glycine residues.

33. The library of claim 1 wherein at least one of said $X^1$, $X^2$, $X^3$ or $X^4$ residues is a cysteine residue.

34. The library of claim 1 further comprising at least one B, said B being a core binding sequence of 1 to 20 amino acid residues in length, and comprising at least one cysteine residue.

35. The library of claim 34 wherein said displayed peptide sequence comprises:

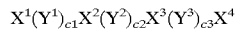

$(C/G)(Y^1)_{c1}(C/G)(Y^2)_{c2}B(C/G)(Y^3)_{c3}(C/G)$ wherein (C/G) is a cysteine or glycine residue.

36. The library of claim 1 wherein the complexity of said library is at least about $10^9$.

37. A method of making said anchor library of claim 1, comprising:

synthesizing a collection of nucleic acid sequences; inserting said nucleic acid sequences into vectors to give recombinant vectors; introducing said recombinant vectors into a host; propagating said host having said recombinant vectors so as to result in a collection of recombinant vectors, each of said recombinant vectors having a nucleic acid sequence from said collection of nucleic acid sequences which encodes a displayed peptide sequence; said displayed peptide sequence comprising:

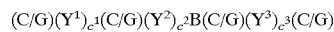

$X^1(Y^1)_{c1}X^2(Y^2)_{c2}X^3(Y^3)_{c3}X^4$ wherein each $X^1$, $X^2$, $X^3$ and $X^4$ is an amino acid residue and any of $X^1$, $X^2$, $X^3$ and $X^4$ can be the same or different from each other, wherein each $Y^1$, $Y^2$ and $Y^3$ is alanine or glycine or a combination of alanine and glycine that is respectively c, $c^2$, and $c^3$ amino acid residues long of any of $Y^1$, $Y^2$ and $Y^3$ can be the same or different from each other, wherein $c^1$, $c^2$ and $c^3$ are 1–20, provided that at least one of $c^1$, $c^2$ and $c^3$ is 3 to 20, and wherein at least about $10^5$ distinct displayed peptide sequences are encoded by said anchor library.

38. The library of claim 37 wherein at least about $10^6$ displayed peptide sequences are present in said anchor library.

39. The library of claim 37 wherein at least about $10^7$ displayed peptide sequences are present in said anchor library.

40. The library of claim 37 wherein at least about $10^8$ displayed peptide sequences are present in said anchor library.

41. The library of claim 37 wherein at least about $10^9$ displayed sequences are present in said anchor library.

42. An anchor library, consisting essentially of:

a collection of recombinant vectors, each of said recombinant vectors having a nucleic acid sequence inserted in a gene, said nucleic acid sequence encoding a displayed peptide sequence, said displayed peptide sequence of each of said vectors comprising

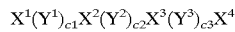

$X^1(Y^1)_{c1}X^2(Y^2)_{c2}X^3(Y^3)_{c3}X^4$ wherein each $X^1$, $X^2$, $X^3$ and $X^4$ is an amino acid residue and any of $X^1$, $X^2$, $X^3$ and $X^4$ can be the same or different from each other, wherein each $Y^1$, $Y^2$, and $Y^3$ is alanine or glycine or a combination of alanine and glycine that is respectively $c^1$, $c^2$ and $c^3$ amino acid residues long and any of $Y^1$, $Y^2$ and $Y^3$ can be the same or different from each other, wherein $c^1$, $c^2$ and $c^3$ are 1–20, provided that at least one of $c^1$, $c^2$ and $c^3$ is 3 to 20, and wherein at least about $10^3$ distinct displayed peptide sequences are encoded by said anchor library.

* * * * *